US008870875B2

(12) United States Patent
Romagnoli et al.

(10) Patent No.: US 8,870,875 B2
(45) Date of Patent: Oct. 28, 2014

(54) GENDER SPECIFIC FEMORAL RASPS

(75) Inventors: Sergio Romagnoli, Savona (IT); Roland Willi, Neftenbach (CH)

(73) Assignee: Zimmer GmbH, Winterthur (CH)

( * ) Notice: Subject to any disclaimer, the term of this patent is extended or adjusted under 35 U.S.C. 154(b) by 840 days.

(21) Appl. No.: 12/179,771

(22) Filed: Jul. 25, 2008

(65) Prior Publication Data
US 2010/0023014 A1  Jan. 28, 2010

(51) Int. Cl.
*A61B 17/00* (2006.01)
*A61B 17/16* (2006.01)

(52) U.S. Cl.
CPC ......... *A61B 17/1659* (2013.01); *A61B 17/1684* (2013.01); *A61B 17/1668* (2013.01)
USPC .......................................................... 606/85

(58) Field of Classification Search
USPC ............................... 606/79, 80–85
See application file for complete search history.

(56) References Cited

U.S. PATENT DOCUMENTS

| 3,815,599 | A | | 6/1974 | Deyerle |
| 4,671,275 | A | | 6/1987 | Deyerle |
| 5,169,402 | A | | 12/1992 | Elloy |
| 5,665,091 | A | * | 9/1997 | Noble et al. ................. 606/85 |
| 5,885,295 | A | | 3/1999 | McDaniel et al. |
| 6,319,256 | B1 | | 11/2001 | Spotorno et al. |
| 6,488,714 | B2 | | 12/2002 | Keller |
| 2004/0249384 | A1 | | 12/2004 | Blaha et al. |
| 2005/0203524 | A1 | * | 9/2005 | Penenberg ................. 606/79 |
| 2005/0234463 | A1 | | 10/2005 | Hershberger et al. |
| 2005/0288676 | A1 | * | 12/2005 | Schnieders et al. ............. 606/79 |
| 2006/0012127 | A1 | | 1/2006 | Noetzli et al. |

FOREIGN PATENT DOCUMENTS

| EP | 0766948 | A2 | 4/1997 |
| EP | 0766948 | A3 | 4/1998 |
| EP | 1106143 | A1 | 6/2001 |
| EP | 1764046 | A2 | 3/2007 |
| EP | 1764046 | A3 | 5/2007 |
| FR | 2961684 | | 12/2011 |

OTHER PUBLICATIONS

"congruent." Collins English Dictionary—Complete & Unabridged 10th Edition. HarperCollins Publishers. Dec. 4, 2012. <Dictionary.com http://dictionary.reference.com/browse/congruent>.*
The partial European Search Report mailed Dec. 4, 2009 in related European patent application No. 09009380.8.

* cited by examiner

*Primary Examiner* — Nicholas Woodall
(74) *Attorney, Agent, or Firm* — Schwegman Lundberg & Woessner, P.A.

(57) ABSTRACT

Rasps for preparing bones of various patients to receive a prosthetic implant and a method for using the same. Multiple rasps may be provided as a set. Within the set, the rasps generally correspond to the size and shape of a single prosthetic implant, such as a prosthetic femoral hip stem, and have a range of bone removal and bone compression capabilities to account for unique bone characteristics of the various patients. A surgeon may select a desired rasp from the set provided depending on the patient's unique bone characteristics.

10 Claims, 15 Drawing Sheets

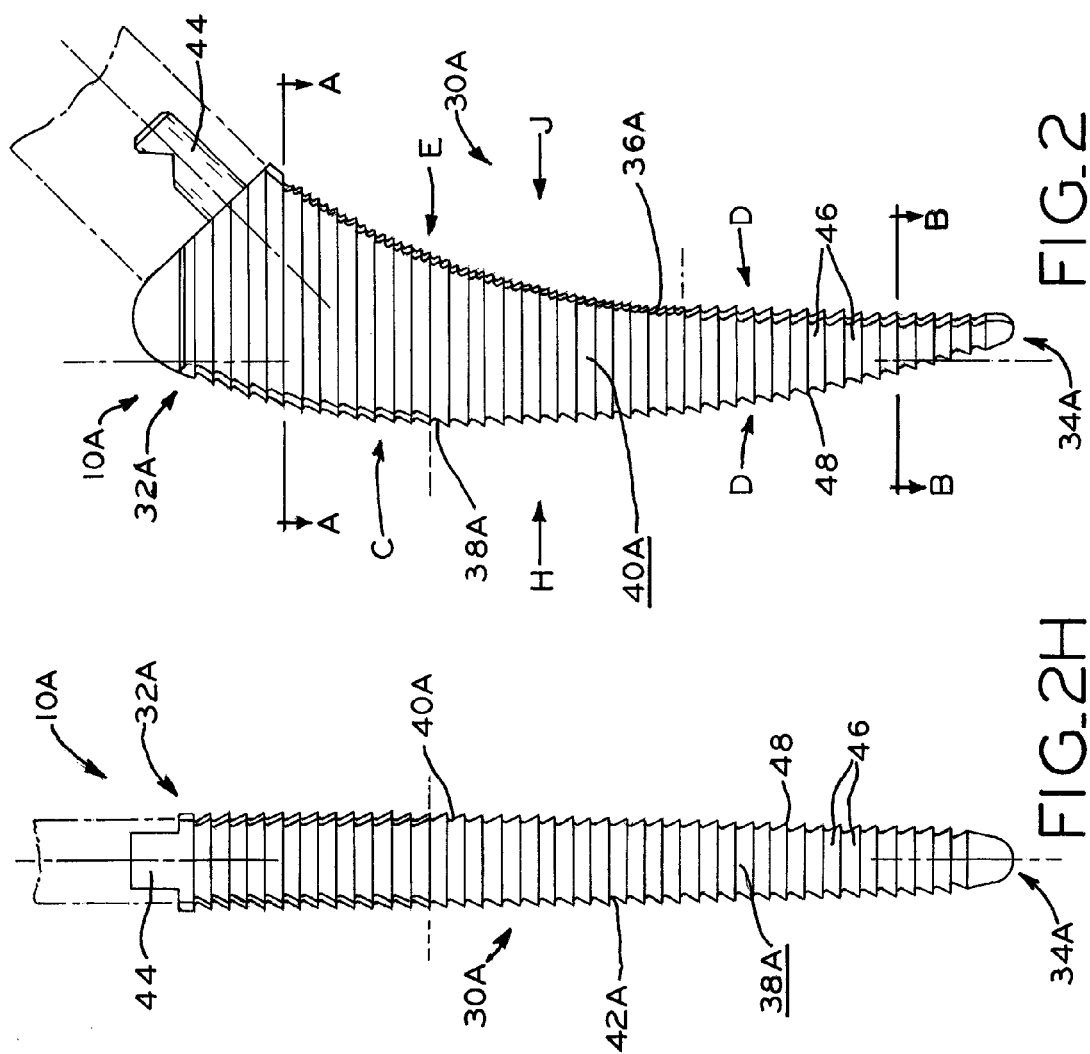

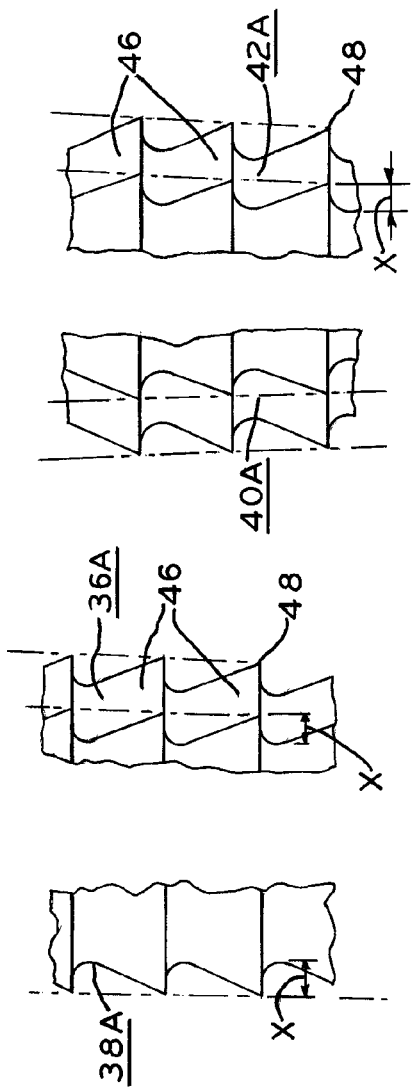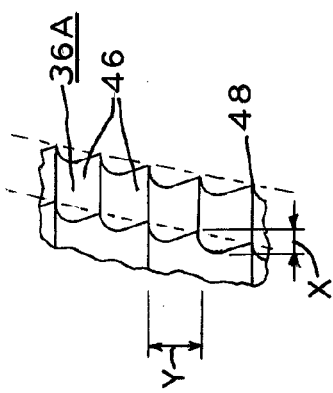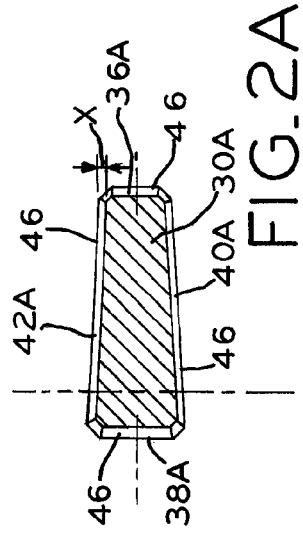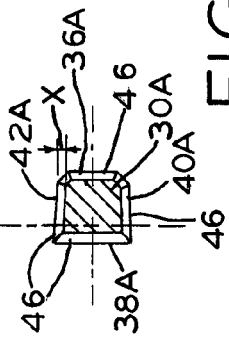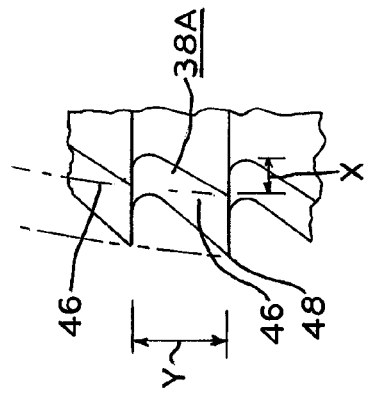
FIG. 2A FIG. 2B FIG. 2C FIG. 2D FIG. 2E FIG. 2G

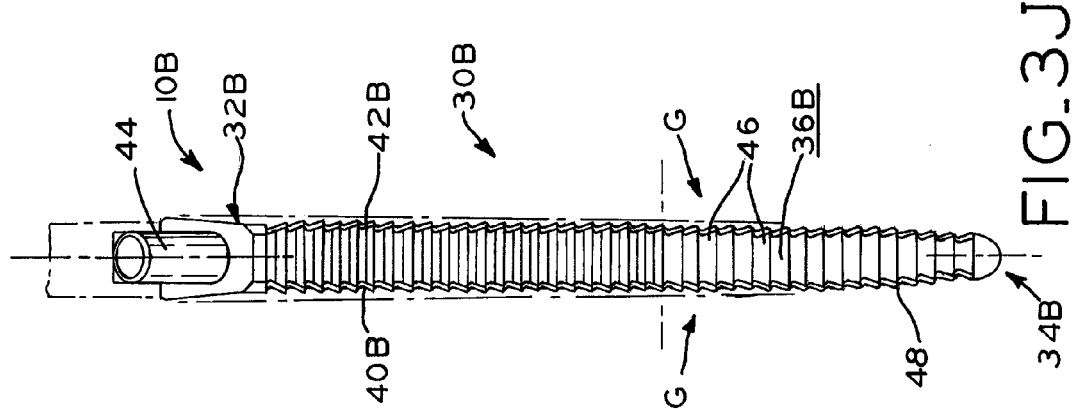
FIG._3J
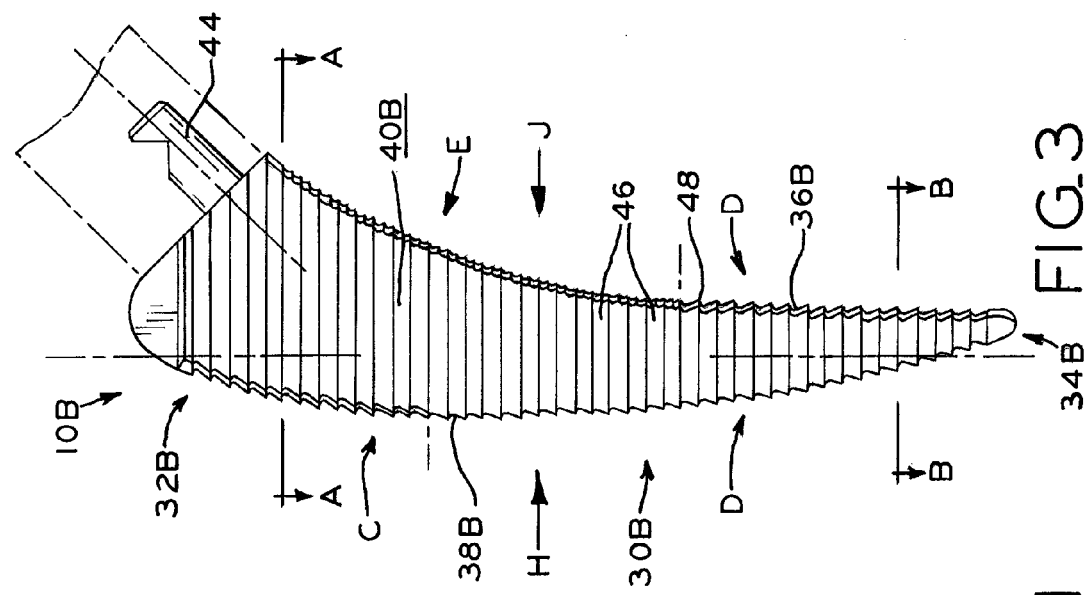
FIG._3
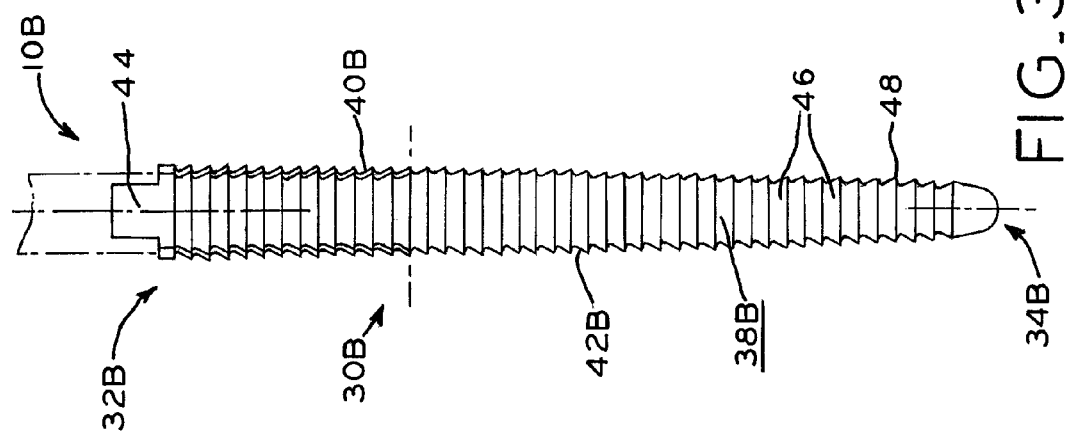
FIG._3H

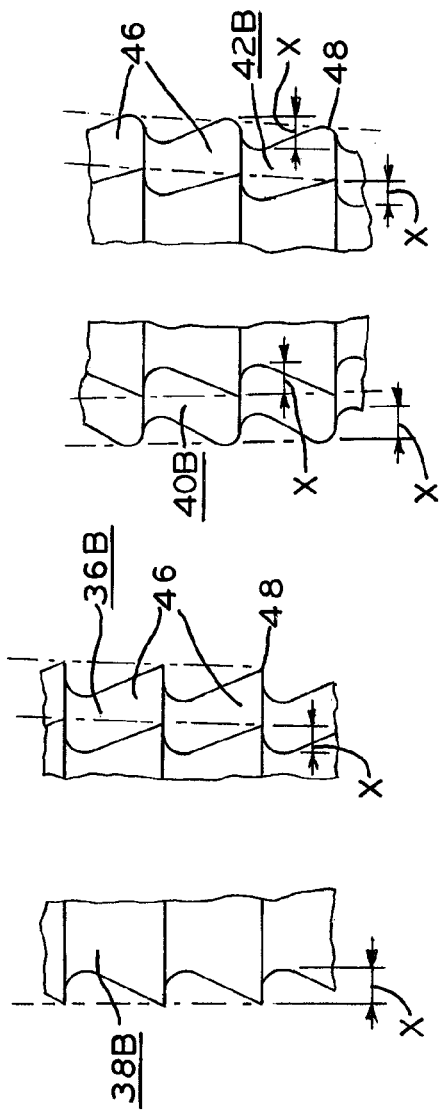

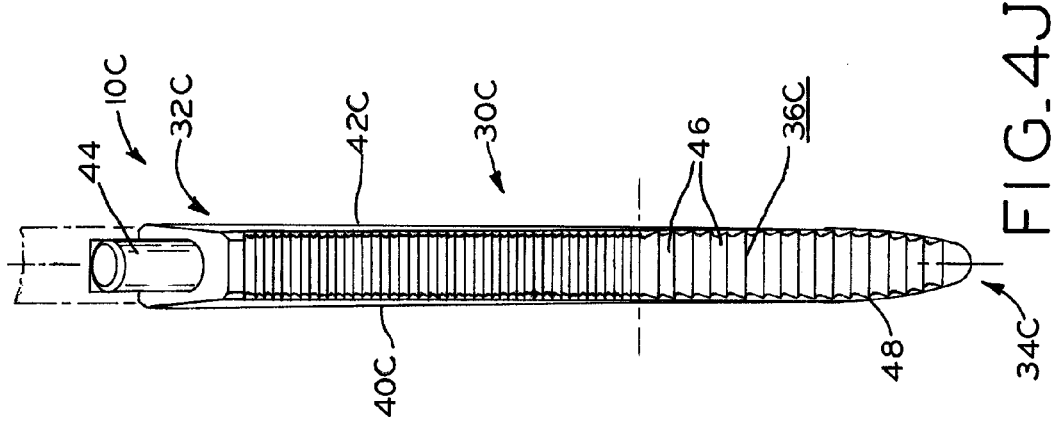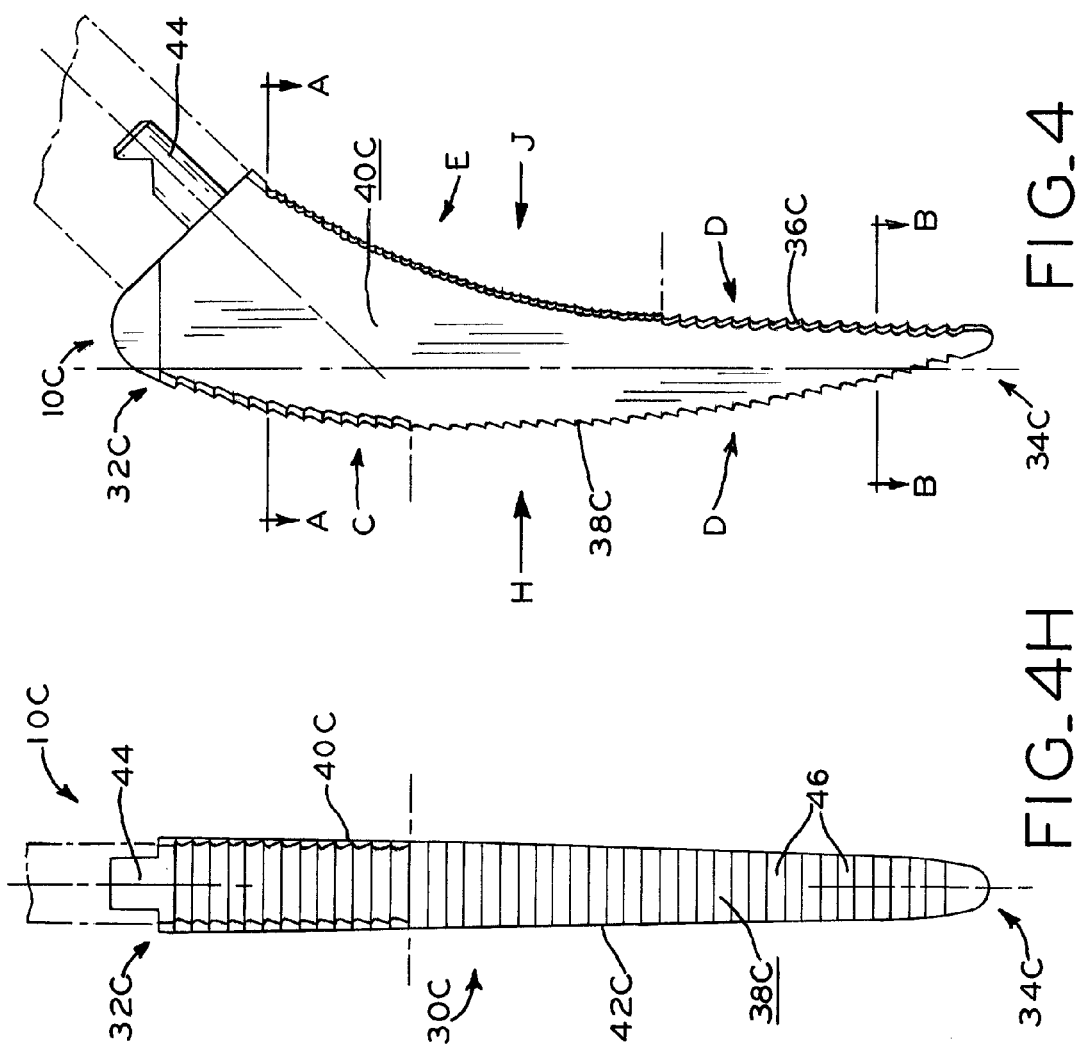

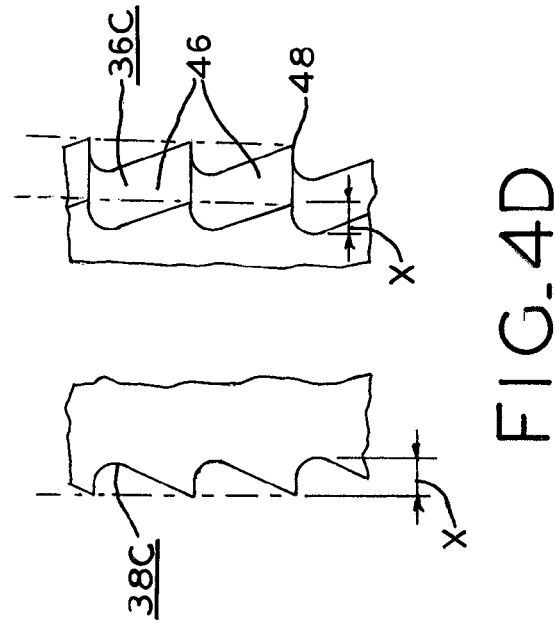
FIG._4D
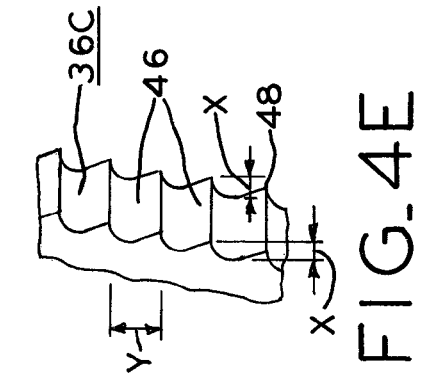
FIG._4E
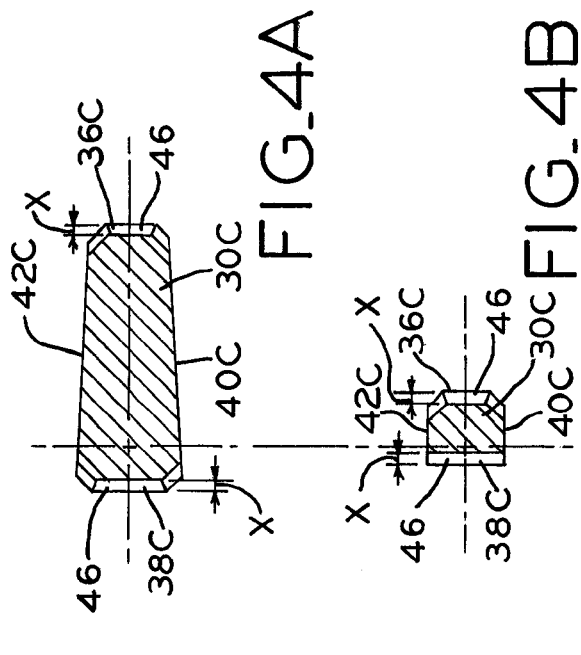
FIG._4A
FIG._4B
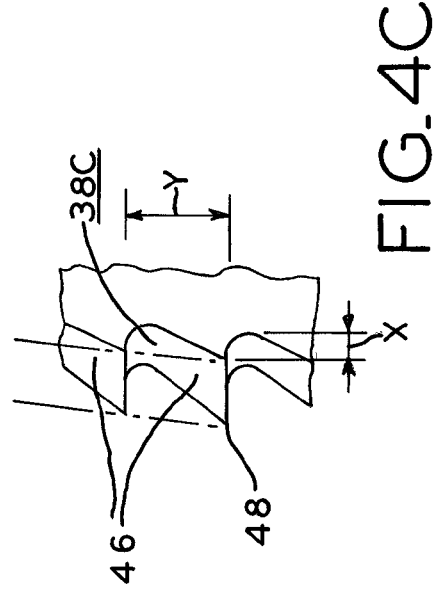
FIG._4C

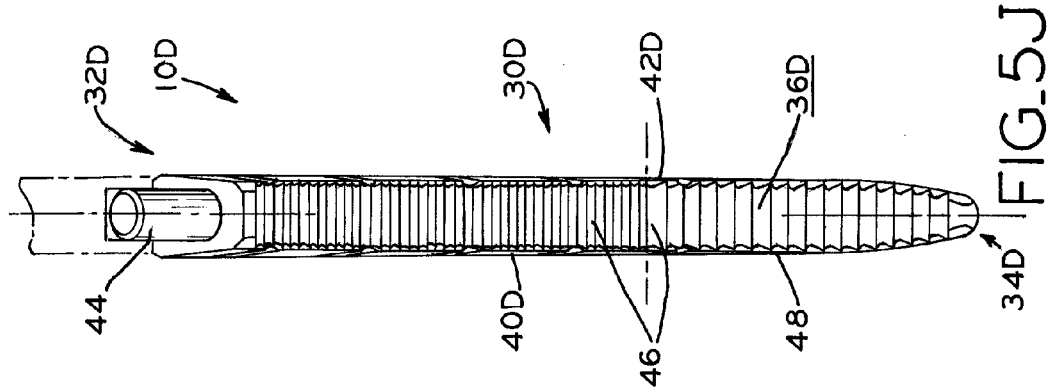
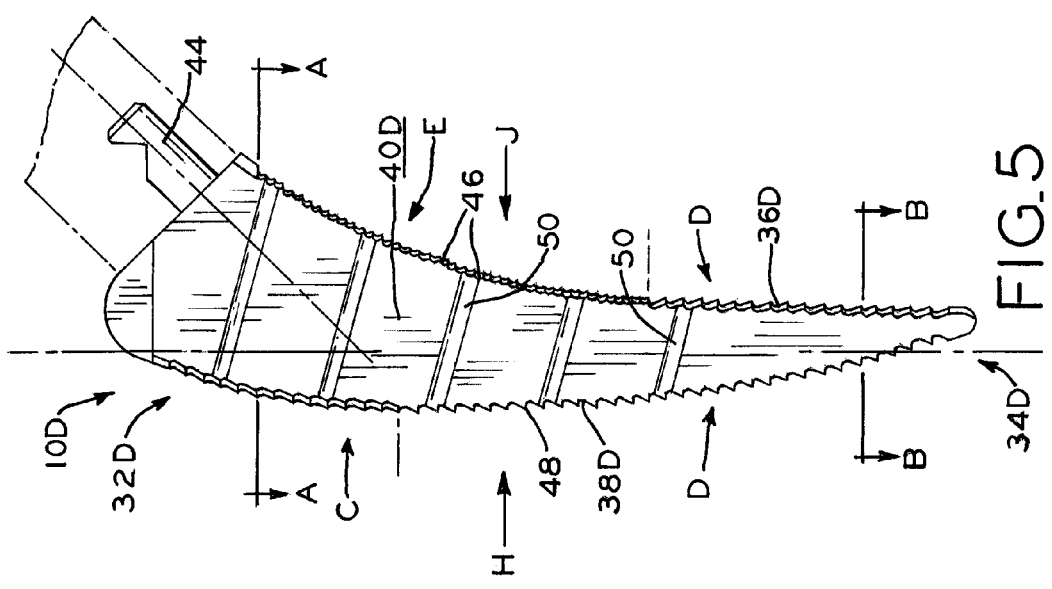
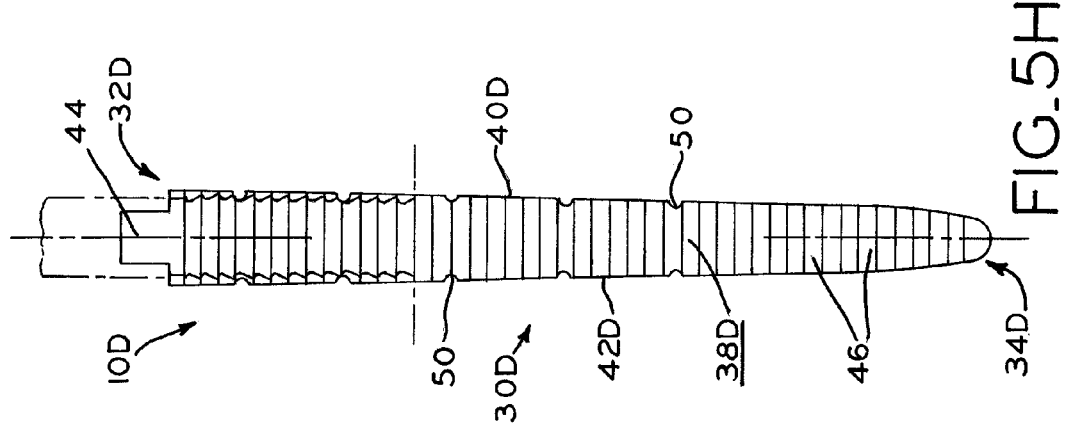

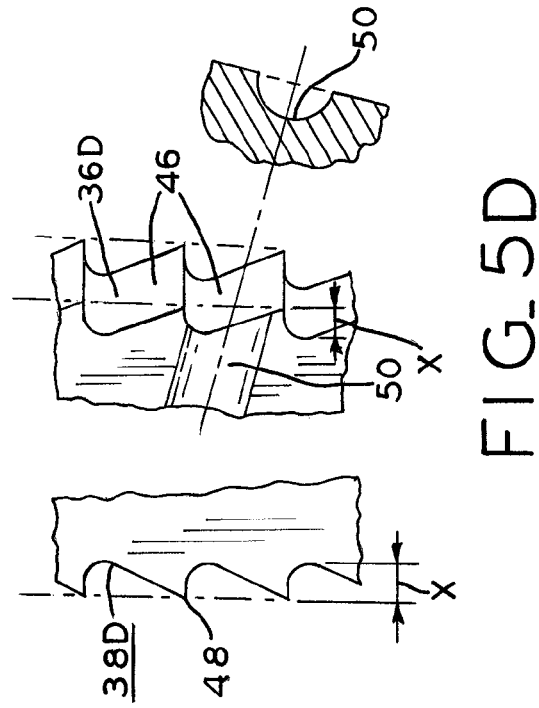
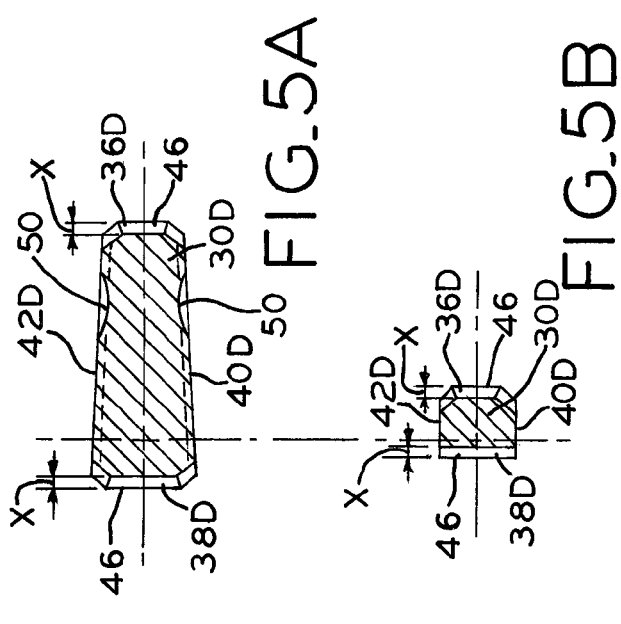

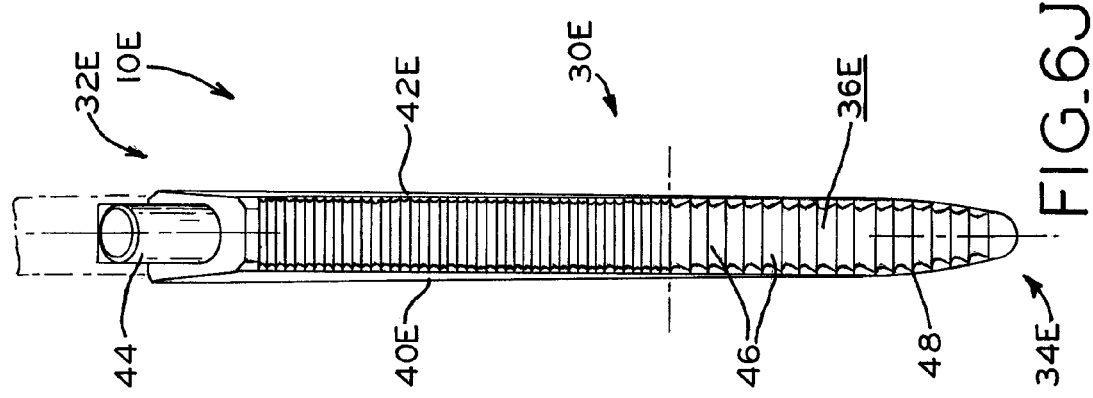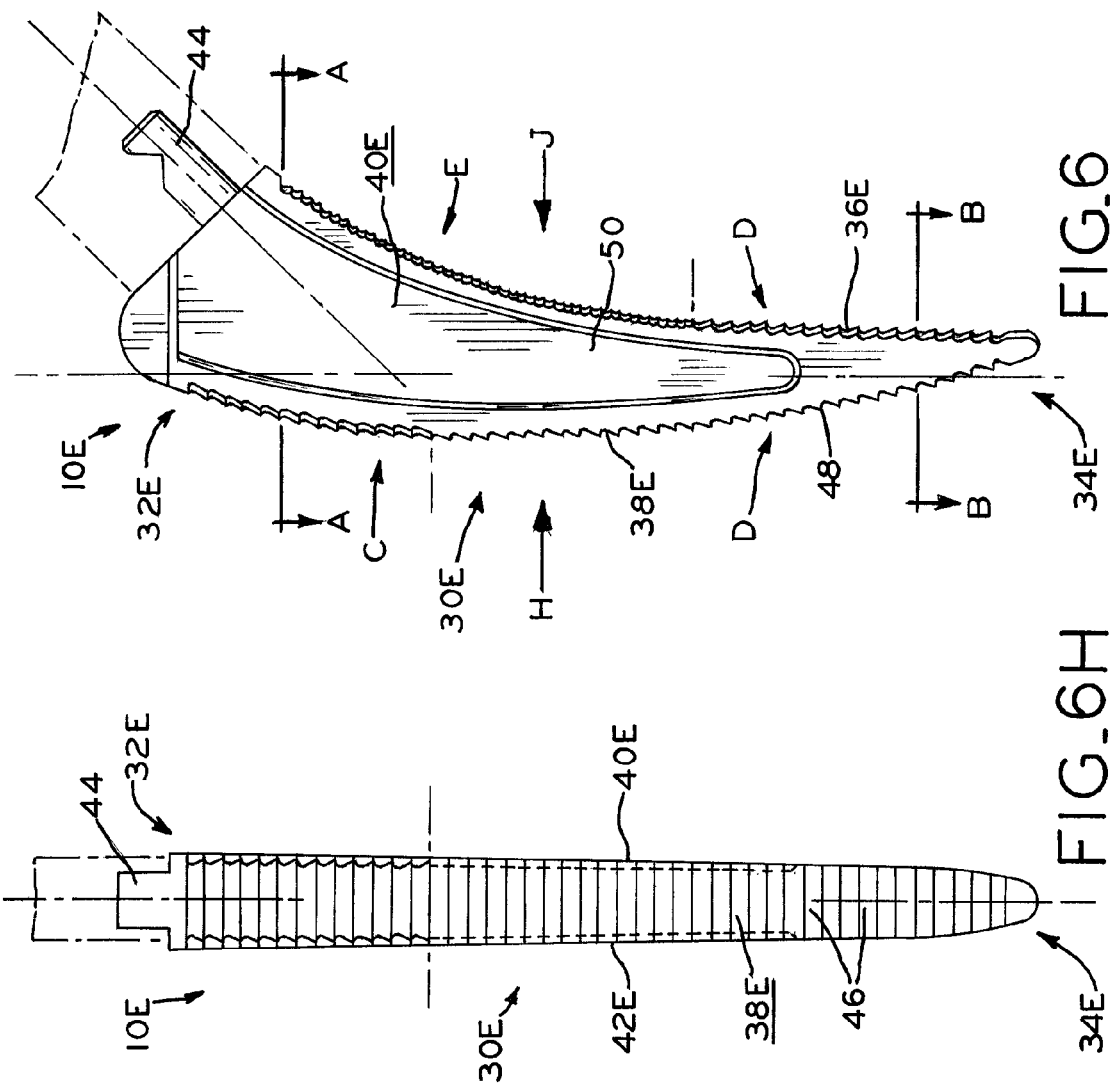

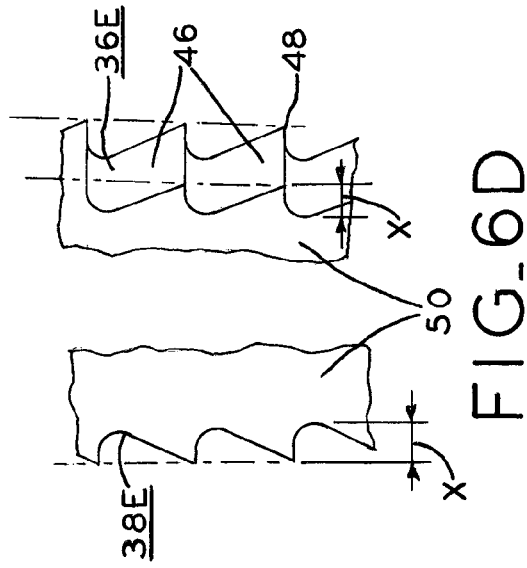
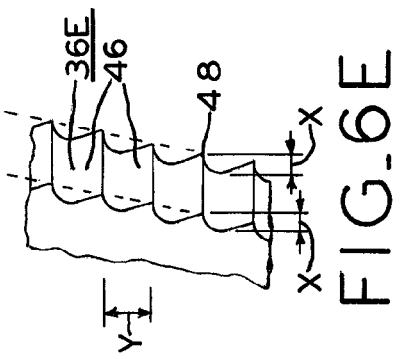
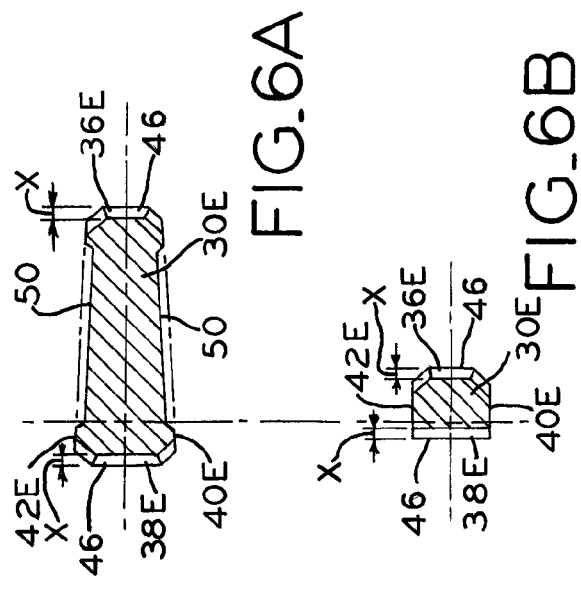
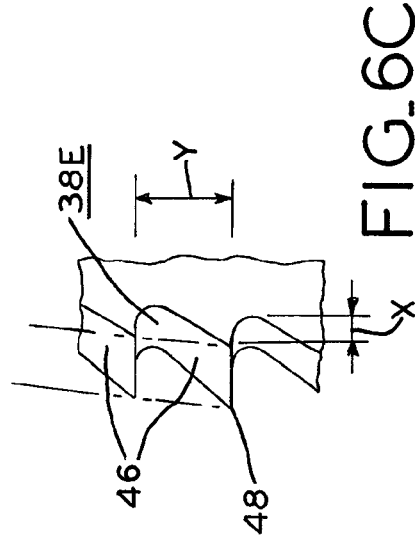

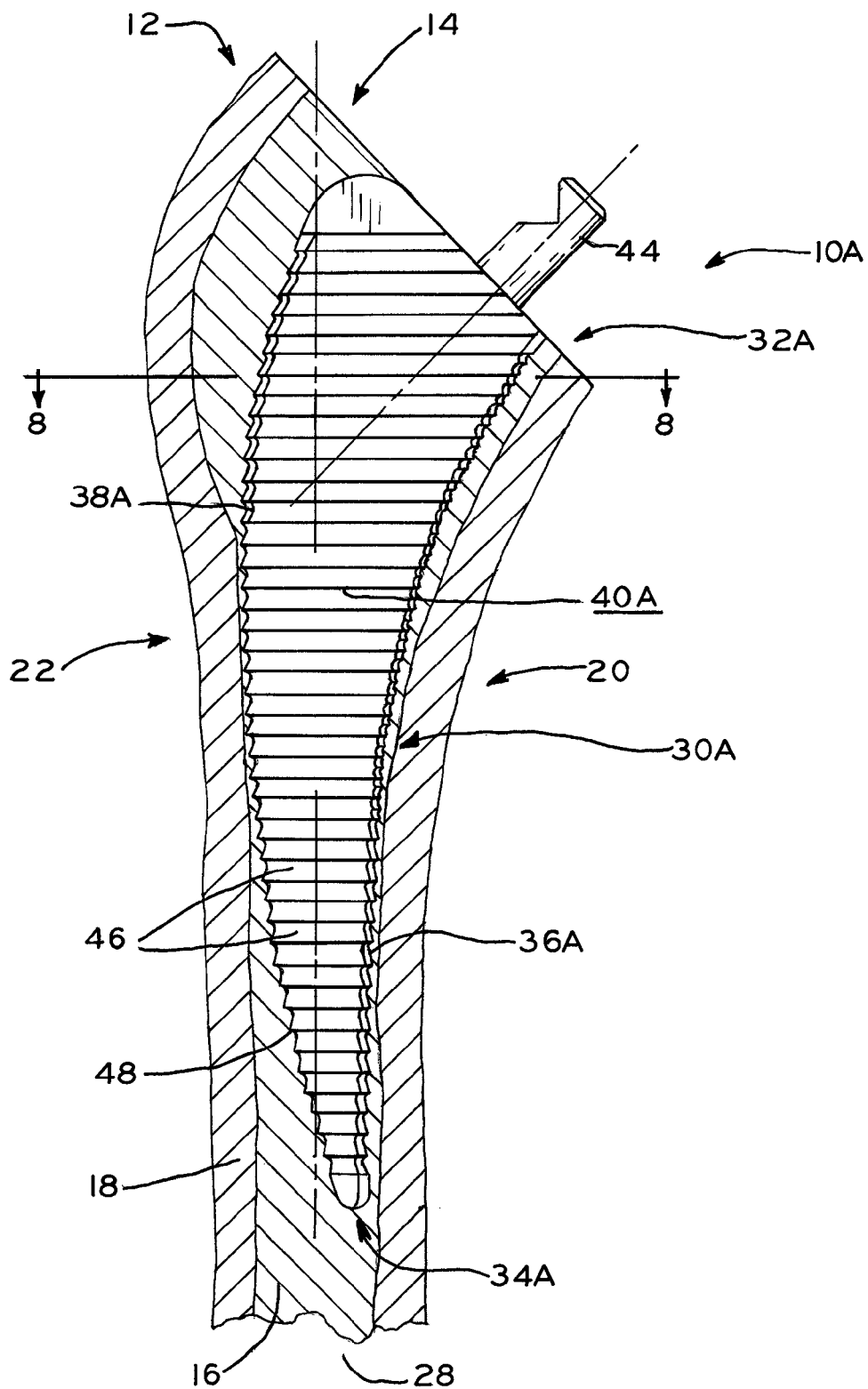
FIG_7

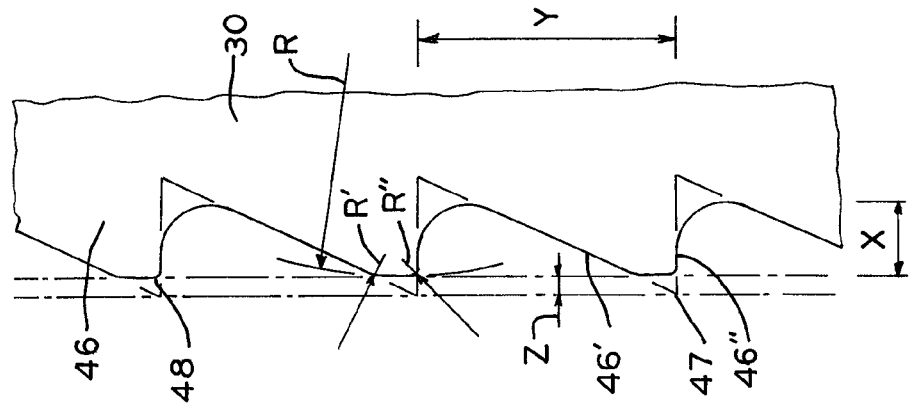
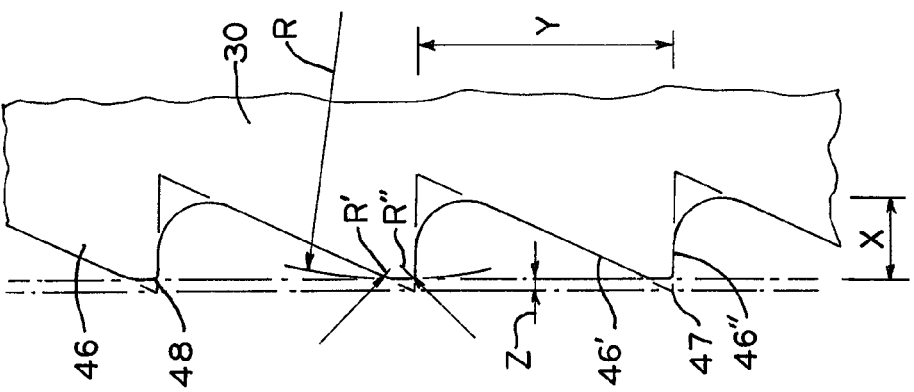
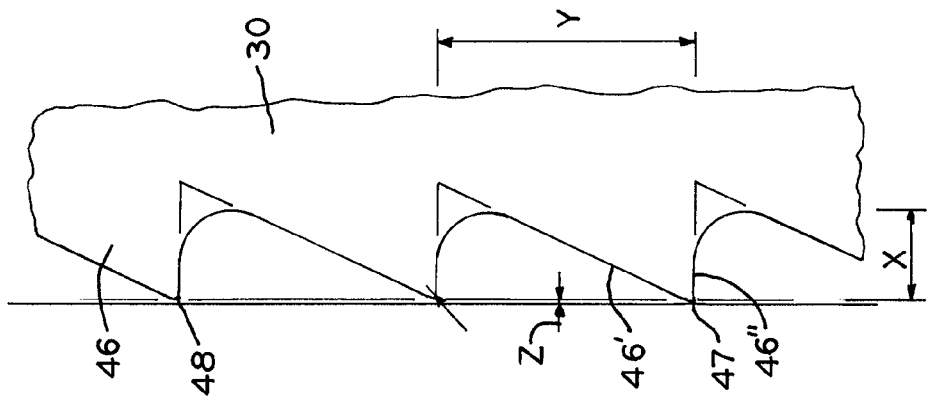

GENDER SPECIFIC FEMORAL RASPS

BACKGROUND

1. Field of the Invention

The present invention relates to rasps. More particularly, the present invention relates to rasps for preparing bones of various patients to receive a prosthetic implant and to a method for using the same.

2. Description of the Related Art

Joint arthroplasty is a surgical procedure for replacing damaged components of a joint with prosthetic components. Such damage may be caused by, for example, traumatic injury or some form of arthritis, such as osteoarthritis. Joint arthroplasty may relieve pain and restore motion in the damaged joint.

The hip joint is formed between the head of the femur and the acetabulum of the pelvis. Therefore, arthroplasty of the hip joint can involve replacing the femoral head and/or the acetabulum with prosthetic implants. Replacing the femoral head, in particular, involves resecting the femoral head along its neck and preparing the intramedullary canal of the femur to receive a prosthetic femoral hip stem. This prosthetic femoral hip stem will ultimately anchor a prosthetic femoral head.

Preparation of the intramedullary canal has a significant impact on the entire arthroplasty procedure. The prepared canal determines the fit between the prosthetic femoral hip stem and the femur, which in turn determines the fit between the prosthetic femoral head and the acetabulum. For example, if the prepared canal is too large, gaps may form between the prosthetic femoral hip stem and the femur, which could cause shifting or rotation of the hip stem. Also, if the prepared canal is too large, the prosthetic femoral hip stem may be seated too deep within the femur, resulting in an unnatural placement of the prosthetic femoral head. On the other hand, if the prepared canal is too small, the prosthetic femoral hip stem may not be seated deep enough within the femur, also resulting in an unnatural placement of the prosthetic femoral head.

Currently, surgeons have available in the operating room a single rasp to prepare the intramedullary canals of each and every patient. This single rasp corresponds to the size and shape of the prosthetic femoral hip stem to be implanted. However, each patient has unique bone characteristics, depending on, for instance, age, health, and gender. Typically, a younger male will have harder, more dense bone than an older female. Therefore, the exact same rasp may result in differently sized canals, depending on the patient's unique bone characteristics. More specifically, the rasp may produce a canal that is too small in a patient with hard, dense bone, while the rasp may produce a canal that is too large in a patient with soft, weak bone.

SUMMARY

The present invention relates to rasps for preparing bones of various patients to receive a prosthetic implant and to a method for using the same. Multiple rasps may be provided as a set. The rasps of the set generally correspond to the size and shape of a single prosthetic implant. Also, the rasps of the set range in aggressiveness to achieve various levels of bone removal and bone compression to account for unique bone characteristics of various patients. The set may include a more aggressive rasp configured to achieve bone removal and a less aggressive rasp configured to achieve bone compression rather than bone removal. For example, a rasp may have sharp, pointed teeth to achieve significant bone removal. Another rasp may have curved, rounded teeth to achieve bone removal, but to a lesser extent than the rasp with pointed teeth. Yet another rasp may have an essentially smooth face to achieve bone compression rather than bone removal. Still yet another rasp may include a groove set into its face to achieve less bone compression than the rasp having an essentially smooth face. A surgeon may select a desired rasp from the set provided depending on the patient's unique bone characteristics.

According to an embodiment of the present invention, a rasp is provided for preparing a bone femur to receive a prosthetic implant. The rasp has an elongate body generally corresponding to the geometry of the prosthetic implant. The elongate body includes a plurality of teeth extending therefrom. The elongate body also includes a medial face, a lateral face, an anterior face, and a posterior face. The medial face has a medial profile generally corresponding to a medial profile of the prosthetic implant, the lateral face has a lateral profile generally corresponding to a lateral profile of the prosthetic implant, the anterior face has an anterior profile generally corresponding to an anterior profile of the prosthetic implant, and the posterior face has a posterior profile generally corresponding to a posterior profile of the prosthetic implant. At least one of the faces is essentially smooth, whereby the essentially smooth face lacks teeth extending therefrom.

According to another embodiment of the present invention, a set of rasps is provided for preparing a bone to receive a prosthetic implant. The set includes a first rasp having a first elongate body and a second rasp having a second elongate body. Both elongate bodies have a geometry generally corresponding to the geometry of the prosthetic implant. The first elongate body includes a medial face having a medial profile generally corresponding to a medial profile of the prosthetic implant, a lateral face having a lateral profile generally corresponding to a lateral profile of the prosthetic implant, an anterior face having an anterior profile generally corresponding to an anterior profile of the prosthetic implant, and a posterior face having a posterior profile generally corresponding to a posterior profile of the prosthetic implant. The anterior face and the posterior face of the first elongate body have at least one of an essentially smooth face, whereby the essentially smooth face lacks teeth extending therefrom, an essentially smooth face with a groove set into and interrupting the essentially smooth face, a plurality of pointed teeth extending therefrom, and a plurality of rounded teeth extending therefrom. Each pointed tooth extends from the face to an end defined between two essentially planar portions of the pointed tooth. Each portion of the pointed tooth is located within a plane, and the planes intersect along an axis. The end of the pointed tooth is located within approximately 0.05 millimeters of the axis. Each rounded tooth extends from the face to an end defined between two essentially planar portions of the rounded tooth. Each portion of the rounded tooth is located within a plane, and the planes intersect along an axis. The end of the rounded tooth is located toward a longitudinal axis of the first elongate body more than approximately 0.05 millimeters from the axis. The second elongate body includes a medial face having a medial profile generally corresponding to the medial profile of the prosthetic implant, a lateral face having a lateral profile generally corresponding to the lateral profile of the prosthetic implant, an anterior face having an anterior profile generally corresponding to the anterior profile of the prosthetic implant, and a posterior face having a posterior profile generally corresponding to the posterior profile of the prosthetic implant. At least one of the anterior face and the posterior face of the second elongate body differs from the corresponding face of the first elongate body.

According to yet another embodiment of the present invention, a set of rasps is provided for preparing a bone to receive a prosthetic implant. The set includes a first rasp having a first elongate body and a second rasp having a second elongate body, both elongate bodies having a geometry generally corresponding to the geometry of the prosthetic implant. The first elongate body includes a proximal end, a distal end, a medial face, a lateral face, an anterior face, and a posterior face. A length of the first elongate body is defined between the proximal end and the distal end of the first elongate body, a width of the first elongate body is defined between the medial face and the lateral face of the first elongate body, and a depth of the first elongate body is defined between the anterior face and the posterior face of the first elongate body. The second elongate body includes a proximal end, a distal end, a medial face, a lateral face, an anterior face, and a posterior face. A length of the second elongate body is defined between the proximal end and the distal end of the second elongate body, a width of the second elongate body is defined between the medial face and the lateral face of the second elongate body, and a depth of the second elongate body is defined between the anterior face and the posterior face of the second elongate body. The length of the second elongate body corresponds to the length of the first elongate body, and the width of the second elongate body corresponds to the width of the first elongate body. Along at least a portion of the corresponding lengths, the depth of the first elongate body exceeds the depth of the second elongate body, such that the first elongate body is configured to contact more bone than the second elongate body.

According to still yet another embodiment of the present invention, a method is provided for preparing a surgical patient's bone to receive a prosthetic implant. The method involves providing at least a first rasp having a first elongate body and a second rasp having a second elongate body, both elongate bodies having a geometry generally corresponding to the geometry of the prosthetic implant. Each elongate body includes a proximal end, a distal end, a medial face, a lateral face, an anterior face, and a posterior face. A length of each elongate body is defined between the proximal end and the distal end of the elongate body. A width of each elongate body is defined between the medial face and the lateral face of the elongate body. A depth of each elongate body is defined between the anterior face and the posterior face of the elongate body. The length of the second elongate body corresponds to the length of the first elongate body, and the width of the second elongate body corresponds to the width of the first elongate body. Along at least a portion of the corresponding lengths, the depth of the second elongate body exceeds the depth of the first elongate body, whereby the second elongate body is configured to contact more bone than the first elongate body. The method also involves rasping the patient's bone with one of the first rasp and the second rasp.

Advantageously, the present invention provides a rasp that allows a surgeon to compress, rather than cut away, the patient's bone. A rasp in this form is especially useful in preparing the bone of a patient having poor bone strength. Also advantageously, by making available a set of rasps, the present invention allows the surgeon to customize preparation of the patient's bone based upon the patient's bone strength.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2 is an anterior plan view of a femoral rasp of the present invention;
FIG. 2A is a cross-sectional view of the femoral rasp of FIG. 2, taken along line A-A of FIG. 2;
FIG. 2B is a cross-sectional view of the femoral rasp of FIG. 2, taken along line B-B of FIG. 2;
FIG. 2C is a partial elevational view of the femoral rasp of FIG. 2, taken along line C of FIG. 2;
FIG. 2D is a partial elevational view of the femoral rasp of FIG. 2, taken along lines D of FIG. 2;
FIG. 2E is a partial elevational view of the femoral rasp of FIG. 2, taken along line E of FIG. 2;
FIG. 2G is a partial elevational view of the femoral rasp of FIG. 2, taken along lines G of FIG. 2J;
FIG. 2H is a lateral plan view of the femoral rasp of FIG. 2, taken along line H of FIG. 2;
FIG. 2J is a medial plan view of the femoral rasp of FIG. 2, taken along line J of FIG. 2;
FIG. 3 is an anterior plan view of another femoral rasp of the present invention;
FIG. 3A is a cross-sectional view of the femoral rasp of FIG. 3, taken along line A-A of FIG. 3;
FIG. 3B is a cross-sectional view of the femoral rasp of FIG. 3, taken along line B-B of FIG. 3;
FIG. 3C is a partial elevational view of the femoral rasp of FIG. 3, taken along line C of FIG. 3;
FIG. 3D is a partial elevational view of the femoral rasp of FIG. 3, taken along lines D of FIG. 3;
FIG. 3E is a partial elevational view of the femoral rasp of FIG. 3, taken along line E of FIG. 3;
FIG. 3G is a partial elevational view of the femoral rasp of FIG. 3, taken along lines G of FIG. 3J;
FIG. 3H is a lateral plan view of the femoral rasp of FIG. 3, taken along line H of FIG. 3;
FIG. 3J is a medial plan view of the femoral rasp of FIG. 3, taken along line J of FIG. 3;
FIG. 4 is an anterior plan view of yet another femoral rasp of the present invention;
FIG. 4A is a cross-sectional view of the femoral rasp of FIG. 4, taken along line A-A of FIG. 4;
FIG. 4B is a cross-sectional view of the femoral rasp of FIG. 4, taken along line B-B of FIG. 4
FIG. 4C is a partial elevational view of the femoral rasp of FIG. 4, taken along line C of FIG. 4;
FIG. 4D is a partial elevational view of the femoral rasp of FIG. 4, taken along lines D of FIG. 4;
FIG. 4E is a partial elevational view of the femoral rasp of FIG. 4, taken along line E of FIG. 4;
FIG. 4H is a lateral plan view of the femoral rasp of FIG. 4, taken along line H of FIG. 4;
FIG. 4J is a medial plan view of the femoral rasp of FIG. 4, taken along line J of FIG. 4;
FIG. 5 is an anterior plan view of yet another femoral rasp of the present invention;
FIG. 5A is a cross-sectional view of the femoral rasp of FIG. 5, taken along line A-A of FIG. 5;
FIG. 5B is a cross-sectional view of the femoral rasp of FIG. 5, taken along line B-B of FIG. 5;
FIG. 5C is a partial elevational view of the femoral rasp of FIG. 5, taken along line C of FIG. 5;
FIG. 5D is a partial elevational view of the femoral rasp of FIG. 5, taken along lines D of FIG. 5;

FIG. 5E is a partial elevational view of the femoral rasp of FIG. 5, taken along line E of FIG. 5;

FIG. 5H is a lateral plan view of the femoral rasp of FIG. 5, taken along line H of FIG. 5;

FIG. 5J is a medial plan view of the femoral rasp of FIG. 5, taken along line J of FIG. 5;

FIG. 6 is an anterior plan view of yet another femoral rasp of the present invention;

FIG. 6A is a cross-sectional view of the femoral rasp of FIG. 6, taken along line A-A of FIG. 6;

FIG. 6B is a cross-sectional view of the femoral rasp of FIG. 6, taken along line B-B of FIG. 6;

FIG. 6C is a partial elevational view of the femoral rasp of FIG. 6, taken along line C of FIG. 6;

FIG. 6D is a partial elevational view of the femoral rasp of FIG. 6, taken along lines D of FIG. 6;

FIG. 6E is a partial elevational view of the femoral rasp of FIG. 6, taken along line E of FIG. 6;

FIG. 6H is a lateral plan view of the femoral rasp of FIG. 6, taken along line H of FIG. 6;

FIG. 6J is a medial plan view of the femoral rasp of FIG. 6, taken along line J of FIG. 6;

FIG. 7 is a partial cross-sectional view of a right femur containing the femoral rasp of FIG. 2;

FIG. 9A is an elevational view of an embodiment of teeth extending from a femoral rasp of the present invention;

FIG. 9B is an elevational view of another embodiment of teeth extending from a femoral rasp of the present invention;

FIG. 9C is an elevational view of yet another embodiment of teeth extending from a femoral rasp of the present invention.

Corresponding reference characters indicate corresponding parts throughout the several views. The exemplifications set out herein illustrate exemplary embodiments of the invention and such exemplifications are not to be construed as limiting the scope of the invention any manner.

DETAILED DESCRIPTION

Figure 1:
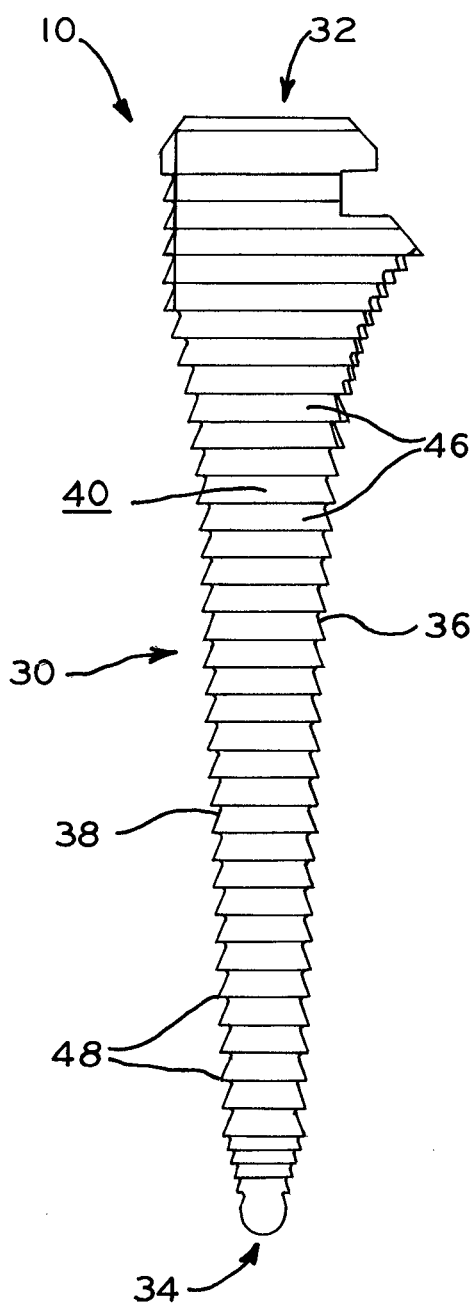
FIG. 1 is an anterior plan view of a femoral rasp.
Figure 1A:
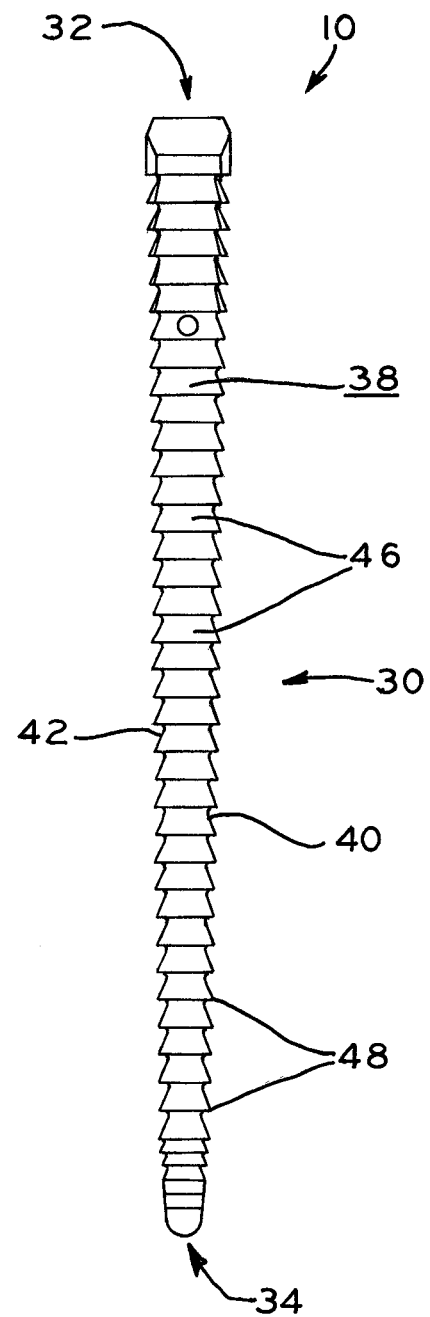
FIG. 1A is a lateral plan view of the femoral rasp of FIG. 1.
Figure 8:
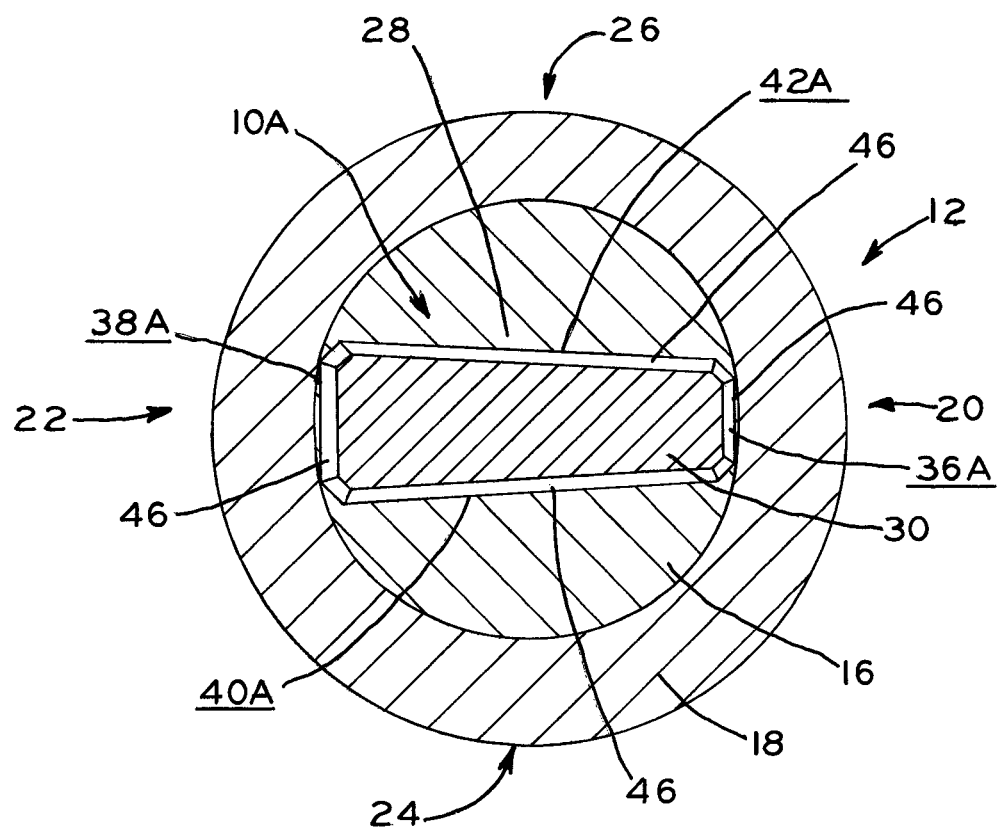
FIG. 8 is a cross-sectional view of the femur and femoral rasp of FIG. 7, taken along line 8-8 of FIG. 7.

Referring to FIGS. 7-8, a rasp of the present invention is shown in the form of femoral rasp 10A within femur 12. The head of femur 12 has been resected from proximal end 14 of femur 12 in preparation for receiving a prosthetic implant in the form of prosthetic femoral hip stem 100 (FIG. 10) that will ultimately anchor a prosthetic femoral head (not shown). Femur 12 includes a soft, spongy layer of trabecular or cancellous bone 16 surrounded by a stronger layer of cortical bone 18. Femur 12 is a long, cylindrical bone that includes medial portion 20, lateral portion 22, anterior portion 24, and posterior portion 26. Intramedullary canal 28 extends the length of femur 12 between medial portion 20, lateral portion 22, anterior portion 24, and posterior portion 26. Although the rasp is described and depicted herein as a femoral rasp configured to prepare a cavity in a femur, the present invention is generally applicable to any device configured to prepare a cavity in trabecular or cancellous bone, such as trabecular or cancellous bone of a tibia or a humerus, for example. Similarly, although the prosthetic implant is described and depicted herein as a prosthetic femoral hip stem, the present invention is generally applicable to any prosthetic implant configured to be worked into a cavity in trabecular or cancellous bone, such as a shaft of a tibial plate, for example.

Figure 10:
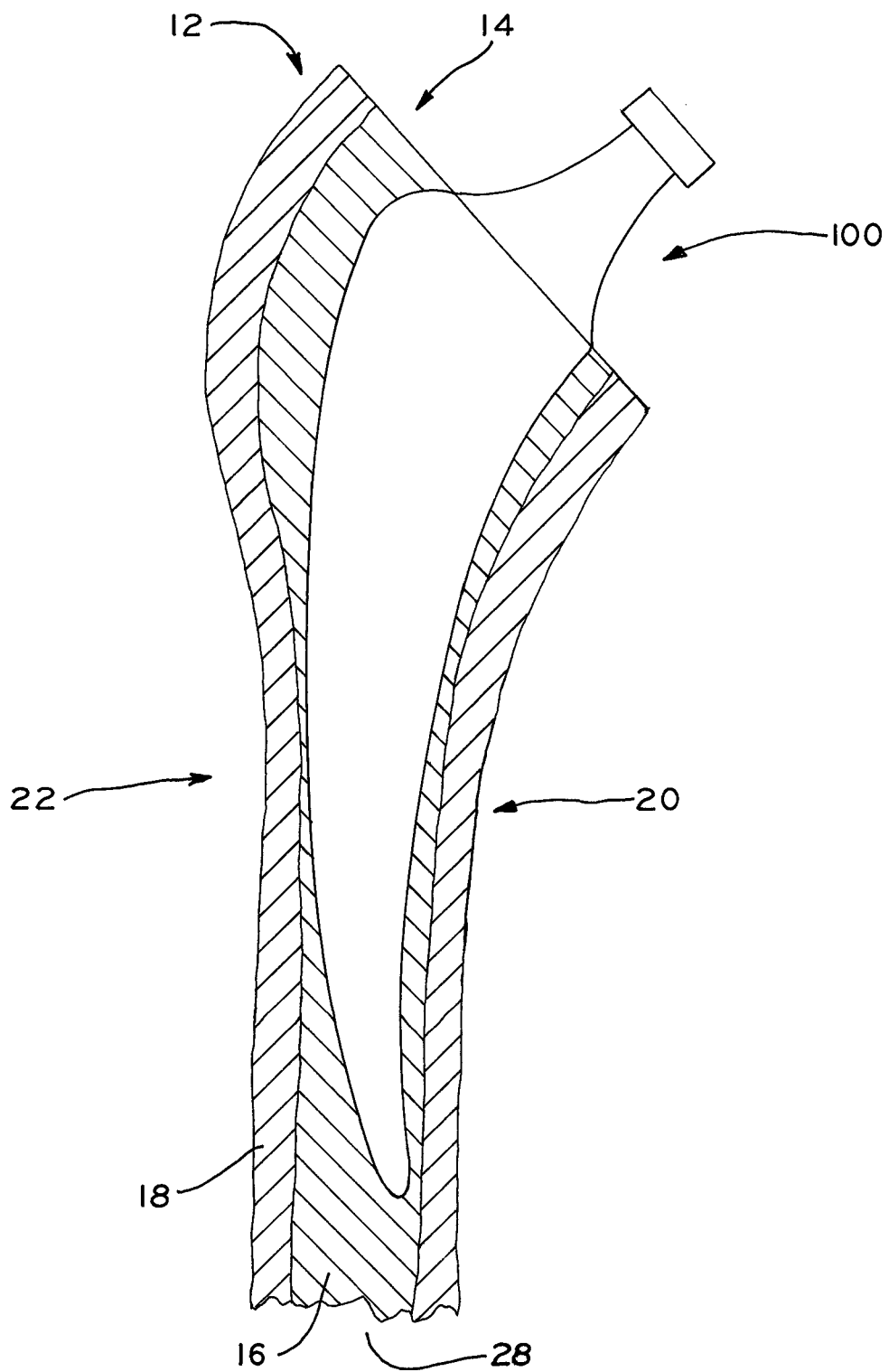
FIG. 10 is a partial cross-sectional view of a right femur containing a prosthetic femoral hip stem.

Referring generally to FIGS. 2-6, rasps 10A-10E of the present invention are illustrated. Referring in particular to FIGS. 2-2J, rasp 10A includes elongate body 30A that generally corresponds to the geometry of prosthetic femoral hip stem 100 to be implanted into femur 12 (FIG. 10). Elongate body 30A extends between proximal end 32A and distal end 34A, and elongate body 30A narrows from proximal end 32A to distal end 34A. Elongate body 30A includes medial face 36A, lateral face 38A, anterior face 40A, and posterior face 42A. As used herein, anterior, posterior, lateral, and medial are determined by the intended use of the rasp to a person having ordinary skill in the art. As shown in FIG. 2A, these faces combine to form elongate body 30A having a trapezoidal cross section. Medial face 36A extends parallel to lateral face 38A, and anterior face 40A is equal in length to posterior face 42A. The width of elongate body 30A, or the distance between medial face 36A and lateral face 38A, exceeds the depth of elongate body 30A, or the distance between anterior face 40A and posterior face 42A. Rasps 10B-10E are illustrated in FIGS. 3-6 and are labeled with reference numerals corresponding to those of rasp 10A. Rasps 10B-10E generally correspond to the geometry of the same prosthetic femoral hip stem 100 (FIG. 10) as rasp 10A.

A femoral rasp generally corresponds to the geometry of a prosthetic femoral hip stem if an outer geometry of the femoral rasp is substantially congruent with an outer geometry of the prosthetic femoral hip stem. The femoral rasp need not be entirely congruent with the prosthetic femoral hip stem. For example, if the prosthetic femoral hip stem will be press fit into femur 12, the outer geometry of the femoral rasp will closely match the outer geometry of the prosthetic femoral hip stem. On the other hand, if the prosthetic femoral hip stem will be cemented into femur 12, the outer geometry of the femoral rasp will slightly exceed the outer geometry of the prosthetic femoral hip stem to clear away enough space for a cement mantle to surround the prosthetic femoral hip stem upon implantation. It is also understood that the outer geometry of the femoral rasp may closely match the outer geometry of the prosthetic femoral hip stem in some locations, but not others, to clear away enough space for the cement mantle in certain desired locations.

As shown in FIGS. 2-6, rasps 10A-10E of the present invention include handle 44. Handle 44 extends from elongate bodies 30A-30E, and more specifically from proximal ends 32A-32E of elongate bodies 30A-30E. Handle 44 provides a location to grip rasps 10A-10E while preparing intramedullary canal 28 of femur 12 (FIG. 7). Handle 44 and elongate bodies 30A-30E may be formed as a single, unitary object, or handle 44 may be a separate piece that is attached to elongate bodies 30A-30E. For additional stability, handle 44 may be embedded into elongate bodies 30A-30E.

Referring again to FIGS. 7-8, during use of rasp 10A to prepare intramedullary canal 28 of femur 12, the respective faces of elongate body 30A correspond to respective portions of femur 12. Specifically, medial face 36A of elongate body 30A corresponds to medial portion 20 of femur 12, lateral face 38A of elongate body 30A corresponds to lateral portion 22 of femur 12, anterior face 40A of elongate body 30A corresponds to anterior portion 24 of femur 12, and posterior face 42A of elongate body 30A corresponds to posterior portion 26 of femur 12. Because the width of elongate body 30A exceeds its depth, rasp 10A will cut deeper into medial portion 20 and lateral portion 22 of femur 12 as compared to anterior portion 24 and posterior portion 26 of femur 12. Therefore, medial face 36A and lateral face 38A of elongate body 30A may contact primarily hard cortical bone 18, while anterior face 40A and posterior face 42A of elongate body 30A may contact primarily soft trabecular bone 16. Rasps 10B-10E of FIGS. 3-6 may also be used to prepare intramedullary canal 28 of femur 12. The respective faces of elongate bodies 30B-30E of rasps 10B-10E would correspond to respective portions of femur 12 as set forth above with respect to rasp 10A.

Referring back to FIGS. 2-6, rasps 10A-10E of the present invention include a plurality of teeth 46. Teeth 46 extend from elongate bodies 30A-30E, and more specifically from medial faces 36A-36E, lateral faces 38A-38E, anterior faces 40A-40E, and/or posterior faces 42A-42E of elongate bodies 30A-30E.

Referring next to FIGS. 9A-9C, each tooth 46 extends outward distance X from elongate body 30 until reaching end 48 at a location furthest from the corresponding face of elongate body 30. As used herein, tooth 46 includes any projection from elongate body 30 in which distance X is greater than or equal to approximately 0.5 millimeters. Distance X may be as large as approximately 1.0 millimeter or 1.5 millimeters, for example. Adjacent teeth 46 are spaced apart by distance Y. In other words, distance Y is equivalent to the distance between ends 48 of adjacent teeth 46. Distance Y may be as small as approximately 1.0 millimeter, 1.5 millimeters, or 2.0 millimeters or as large as approximately 2.5 millimeters, 3.0 millimeters, or more, for example. Distances X and Y impact the amount of bone cut away by teeth 46. For example, as distance X increases, teeth 46 project further away from elongate body 30 and further into the bone. According to an exemplary embodiment of the present invention, a ratio of distance X to distance Y for each tooth 46 may range between 1:2 and 1:3, for example.

Referring still to FIGS. 9A-9C, the shape of teeth 46, and in particular ends 48, also impacts the amount of bone cut away by teeth 46. Each tooth 46 includes two essentially planar portions, referred to herein as top portion 46' and bottom portion 46". It is within the scope of the present invention that essentially planar top portion 46' and bottom portion 46" of tooth 46 may be partially or entirely arcuate. As shown in FIGS. 9A-9C, top portion 46' extends distally from elongate body 30 toward bottom portion 46" at an acute angle from a longitudinal axis of elongate body 30. For example, top portion 46' may extend distally from elongate body 30 toward bottom portion 46" at an angle of approximately 30 degrees from the longitudinal axis. Bottom portion 46" extends from elongate body 30 generally perpendicularly to the longitudinal axis of elongate body 30. The planes containing top portion 46' and bottom portion 46" intersect along axis 47. End 48 of tooth 46 is defined between top portion 46' and bottom portion 46" and is spaced distance Z from axis 47.

In one form of the present invention, illustrated in FIG. 9A, end 48 is pointed. As used herein, end 48 of tooth 46 is "pointed" when distance Z is less than or equal to approximately 0.05 millimeters. Therefore, if top portion 46' and bottom portion 46" of tooth 46 extend nearly to axis 47, such that end 48 forms within 0.05 millimeters of axis 47, tooth 46 is considered pointed. Tooth 46 may also be considered pointed if top portion 46' and bottom portion 46" of tooth 46 extend slightly beyond axis 47, such that end 48 forms within 0.05 millimeters of axis 47.

In another form of the present invention, illustrated in FIGS. 9B-9C, end 48 is rounded. As used herein, end 48 of tooth 46 is "rounded" when end 48 fails to extend to axis 47 and distance Z is greater than approximately 0.05 millimeters. End 48 may be a linear segment of tooth 46 joining top portion 46' and bottom portion 46", or end 48 may be a curved segment of tooth 46 having a radius of curvature R. In an exemplary embodiment of the present invention, radius of curvature R approaches infinity between top portion 46' and bottom portion 46", and radii of curvature R' and R" decrease as end 48 joins top portion 46' and bottom portion 46", respectively.

Referring still to FIGS. 2-6, rasps 10A-10E are provided with elongate bodies 30A-30E having identical medial faces 36A-36E and identical lateral faces 38A-38E. As shown in FIGS. 2J, 3J, 4J, 5J, and 6J, medial faces 36A-36E of elongate bodies 30A-30E include teeth 46 having sharp, pointed ends 48. As shown by comparing FIGS. 2E and 2D, teeth 46 are spaced closer together near proximal end 32A of elongate body 30A (FIG. 2E) than near distal end 34A of elongate body 30A (FIG. 2D). In other words, distance Y may increase from proximal end 32A to distal end 34A. This varied distance Y is also illustrated in FIGS. 3D-3E, 4D-4E, 5D-5E, and 6D-6E for rasps 10B-10E. As shown in FIGS. 2H, 3H, 4H, 5H, and 6H, lateral faces 38A-38E of elongate bodies 30A-30E also include teeth 46 having sharp, pointed ends 48. As shown by comparing FIGS. 2C and 2D, teeth 46 extend outward from lateral face 38A more near proximal end 32A of elongate body 30A (FIG. 2C) than near distal end 34A of elongate body 30A (FIG. 2D). In other words, distance X may decrease from proximal end 32 to distal end 34. This varied distance X is also illustrated in FIGS. 3C-3D, 4C-4D, 5C-5D, and 6C-6D for rasps 10B-10E.

Referring still to FIGS. 2-6, rasps 10A-10E are provided with elongate bodies 30A-30E having different anterior faces 40A-40E and different posterior faces 42A-42E. As discussed above and as illustrated in FIG. 8, anterior and posterior faces, 40A and 42A, of rasp 10A may contact more trabecular bone 16 of femur 12 than medial and lateral faces, 36A and 38A, of rasp 10A, which may contact more cortical bone 18 of femur 12. Additionally, the strength of bone varies from patient to patient depending on, for example, each patient's age, health, and gender. For example, it has been observed that in females, and particularly in females with osteoporosis, intramedullary canal 28 tends to widen in anterior portion 24 and posterior portion 26 of femur 12, resulting in weakened anterior portion 24 and posterior portion 26 of femur 12 compared to medial portion 20 and lateral portion 22 of femur 12. Therefore, in an exemplary embodiment of the present invention, rasps 10A-10E are provided having various anterior faces 40A-40E and various posterior faces 42A-42E. However, the following discussion is not to be limited to anterior and posterior faces, 40A-40E and 42A-42E, of elongate bodies 30A-30E. In accordance with the teachings herein, the following discussion may be adapted to medial faces 36A-36E and/or lateral faces 38A-38E of elongate bodies 30A-30E.

According to an embodiment of the present invention, illustrated in FIGS. 2-2J, anterior face 40A and posterior face 42A of elongate body 30A include teeth 46 having sharp, pointed ends 48. In this embodiment, anterior face 40A and posterior face 42A are similar to medial face 36A and lateral face 38A, all having teeth 46 with sharp, pointed ends 48. Teeth 46 on anterior and posterior faces, 40A and 42A, are shown in detail in FIG. 2G. In this form, rasp 10A is capable of cutting away a significant amount of bone from anterior portion 24 and posterior portion 26 of femur 12.

According to another embodiment of the present invention, illustrated in FIGS. 3-3J, anterior face 40B and posterior face 42B of elongate body 30B include teeth 46 having curved, rounded ends 48. Teeth 46 on anterior and posterior faces, 40B and 42B, are shown in detail in FIG. 3G. In this form, rasp 10B is capable of cutting away bone from anterior portion 24 and posterior portion 26 of femur 12, but not as much bone as the prior embodiment of rasp 10A (FIG. 2) having teeth 46 with sharp, pointed ends 48.

According to yet another embodiment of the present invention, illustrated in FIGS. 4-4J, anterior face 40C and posterior face 42C of elongate body 30C are essentially smooth. As used herein, "essentially smooth" means that the face of elongate body 30C lacks teeth 46 extending therefrom. In this form, rasp 10C will compress bone in anterior portion 24 and posterior portion 26 of femur 12 rather than cutting away bone.

According to still yet another embodiment of the present invention, illustrated in FIGS. 5-5J, anterior face 40D and posterior face 42D of elongate body 30D include several grooves 50 that extend into elongate body 30D. In this form, rasp 10D will compress bone in anterior portion 24 and posterior portion 26 of femur 12 rather than cutting away bone. Due to grooves 50 being set back from anterior face 40D and posterior face 42D of elongate body 30D, rasp 10D may compress even less bone than rasp 10C (FIG. 4) because rasp 10D is more narrow than rasp 10C along groove 50. More specifically, the depth of rasp 10D, or the distance between anterior face 40D and posterior face 42D, along groove 50 is less than the depth of rasp 10C, or the distance between anterior face 40C and posterior face 42C (FIG. 4), without groove 50.

According to still yet another embodiment of the present invention, illustrated in FIGS. 6-6J, anterior face 40E and posterior face 42E of elongate body 30E include grooves 50 that extend into elongate body 30E and span the length of elongate body 30E. Specifically, grooves 50 in this embodiment span anterior face 40E and posterior face 42E of elongate body 30E. In this form, rasp 10E will compress bone in anterior portion 24 and posterior portion 26 of femur 12 rather than cutting away bone. Due to grooves 50 spanning anterior face 40E and posterior face 42E of elongate body 30E, rasp 10E may compress even less bone than rasp 10D (FIG. 5) because rasp 10E is more narrow than rasp 10D across nearly the entire length of rasp 10E.

This disclosure is intended to cover combinations and adaptations of the embodiments discussed above. For example, it is within the scope of this disclosure that medial face 36 and/or lateral face 38 of elongate body 30 may include teeth 46 having curved, rounded ends 48. Similarly, it is within the scope of this disclosure that medial face 36 and/or lateral face 38 of elongate body 30, or at least a portion thereof, may be essentially smooth. It is also within the scope of this disclosure that anterior face 40 may differ from posterior face 42 of elongate body 30. For example, anterior face 40 may be essentially smooth, while posterior face 42 may include several grooves 50. It is also within the scope of this disclosure that medial face 36, lateral face 38, anterior face 40, and/or posterior face 42 of elongate body 30 may vary along a length of the rasp between the proximal end and the distal end of the rasp.

According to an embodiment of the present invention, a set of more than one rasp may be provided, each rasp having unique features. The rasps of the set may be configured, suited, and intended to be used to prepare a bone for the implantation of one and the same prosthetic implant. Therefore, the rasps of the set may have identical basic geometries, but the rasps may have different cutting properties. The cutting properties of the rasps may be determined by, for example, the presence, elevation, number, sharpness, and/or pointedness, of cutting elements or teeth. These varied cutting properties within the set are purposeful, systematic, and intentional, as opposed to arbitrary differences in cutting properties that may result from wear and/or manufacturing tolerances.

In an exemplary embodiment, the set includes numerous rasps that range in aggressiveness to achieve various levels of bone removal and bone compression to account for unique bone characteristics of various patients, such as rasps 10A-10E illustrated in FIGS. 2-6. For example, the set may include a more aggressive rasp configured to achieve bone removal, such as rasp 10A having sharp, pointed teeth 46 (FIG. 2) or rasp 10B having curved, rounded teeth 46 (FIG. 3). The set may also include a less aggressive rasp configured to achieve bone compression rather than bone removal, such as rasp 10C having essentially smooth surfaces (FIG. 4) or rasp 10D or 10E having grooves 50 (FIGS. 5-6).

In another exemplary embodiment, the set includes at least a first rasp and a second rasp. The first rasp may have a more aggressive cutting surface than the second rasp, at least over a portion of the corresponding cutting surfaces. The second rasp may have a cutting surface that varies from the aggressive cutting surface of the first rasp, at least over the corresponding portion of the second rasp. For example, over at least corresponding portions of the first and second rasps, the first rasp may have cutting elements of higher elevation than the cutting elements of the second rasp. As another example, over at least corresponding portions of the first and second rasps, the first rasp may have more cutting elements than the second rasp. As yet another example, over at least corresponding portions of the first and second rasps, the first rasp may include cutting elements, and the second rasp may include an essentially smooth surface and/or an essentially smooth surface with grooves set therein. Further ways to vary the cutting properties of the first and second rasps are described throughout this specification and the claims.

In yet another exemplary embodiment, the set includes at least a first rasp and a second rasp. Each rasp includes faces and edges defined between the faces, such as medial face 36A, lateral face 38A, anterior face 40A, and posterior face 42A of rasp 10A and the edges defined between those faces (FIG. 2). The cutting properties of the first and second rasps may be essentially identical at the edges, but the cutting properties may vary over at least a portion of corresponding faces. For example, the first and second rasps may have identical cutting properties at their edges, but the first rasp may have a more aggressive cutting surface than the second rasp, at least over a portion of the corresponding faces. In a further exemplary embodiment, the first rasp may have a more aggressive anterior and/or posterior cutting surface than the second rasp, at least over a portion of the corresponding faces, while the first and second rasps may have identical cutting properties over corresponding portions of their lateral and/or medial faces.

In still yet another exemplary embodiment, the set includes at least a first rasp and a second rasp. The cutting properties of the first and second rasps may be essentially identical over portions of the rasps intended to cut cortical bone. However, the cutting properties of the first and second rasps may vary, at least in part, over portions of the rasps intended to cut cancellous or trabecular bone.

Referring to FIGS. 7-8, a method is provided for using rasp 10 to prepare intramedullary canal 28 of a patient's femur 12. A first step of the present method involves providing a set of more than one rasp, as described in more detail above. Each rasp of the set may differ from the others. In an exemplary form of the present method, the set includes numerous rasps having a range of bone removal and bone compression capabilities, such as rasps 10A-11E illustrated in FIGS. 2-6.

Another step of the present method involves evaluating the strength of the patient's bones. The surgeon may perform a physical evaluation of the patient's bones, or base his determination of bone strength on the patient's age, health, gender, or any other relevant factors. For example, the surgeon may determine that a younger male patient will have harder, more dense bone than an older female patient.

After the surgeon has evaluated the strength of the patient's bones, the present method involves selecting a desired rasp from the set provided based upon the needs of the patient. In an exemplary form of the present method, this step involves selecting a desired rasp from a set that includes numerous rasps having a range of bone removal and bone compression capabilities, such as rasps 10A-10E illustrated in FIGS. 2-6. Therefore, the surgeon may select a desired rasp based upon the strength of a particular patient's bones and the amount of bone removal and/or bone compression necessary to prepare femur 12. For example, if the patient has strong bones or high bone density, the surgeon may need to cut away bone from femur 12 to prepare intramedullary canal 28 (FIGS. 7-8). Attempting to prepare intramedullary canal 28 in strong bone using an essentially smooth rasp 10C (FIG. 4) would be difficult. Therefore, the surgeon could select from the set rasp 10A having sharp, pointed teeth 46 (FIG. 2) or rasp 10B having curved, rounded teeth 46 (FIG. 3). On the other hand, if the patient has weak bones or low bone density, the surgeon may need to compress bone in femur 12 to prepare intramedullary canal 28 (FIGS. 7-8). By compressing or compacting bone in femur 12, prosthetic femoral hip stem 100 (FIG. 10) may be surrounded by bone that is actually stronger than it was prior to rasping. Cutting away this soft bone, rather than compressing it, could remove too much bone from femur 12, resulting in prepared intramedullary canal 28 that is too large for prosthetic femoral hip stem 100 (FIG. 10). Therefore, the surgeon could select from the set rasp 10C having essentially smooth surfaces (FIG. 4) or rasp 10D or 10E having grooves 50 (FIGS. 5-6). Advantageously, this exemplary embodiment allows a surgeon to customize preparation of femur 12 to the needs of a particular patient.

Referring again to FIGS. 7-8, another step of the present method involves rasping intramedullary canal 28 of the patient's femur 12 with the desired rasp, illustrated as rasp 10A. First, the surgeon orients rasp 10A with respect to femur 12 such that medial face 36A of elongate body 30A corresponds to medial portion 20 of femur 12, lateral face 38A of elongate body 30A corresponds to lateral portion 22 of femur 12, anterior face 40A of elongate body 30A corresponds to anterior portion 24 of femur 12, and posterior face 42A of elongate body 30A corresponds to posterior portion 26 of femur 12. Next, distal end 34A of rasp 10A is driven into femur 12, which may require the use of a tool such as a hammer. Then, the surgeon grips handle 44 and moves rasp 10A up and down in a sawing motion within femur 12 until rasp 10A is seated sufficiently deep within femur 12. Finally, rasp 10A is removed from femur 12. According to an exemplary embodiment of the present invention, anterior face 40A and posterior face 42A contact primarily trabecular bone 16 of femur 12, while medial face 36A and lateral face 38A contact primarily cortical bone 18 of femur 12.

Referring to FIG. 10, a final step of the present method involves implanting prosthetic femoral hip stem 100 into the prepared intramedullary canal 28 of the patient's femur 12. By providing a set of rasps as set forth above, the prosthetic implant should fit securely in the bone, such as by press-fit, independent of the patient's unique bone characteristics and bone quality. For example, prosthetic femoral hip stem 100 should fit securely into the prepared intramedullary canal 28 of femur 12. Proper placement of prosthetic femoral hip stem 100 is necessary for proper placement of the prosthetic femoral head (not shown), and proper placement of the prosthetic femoral head is necessary to achieve natural interaction with the acetabulum (not shown). Prosthetic femoral hip stem 100 itself may be designed to accommodate the patient's particular anatomy and bone strength, depending on, for example, the patient's age, health, and gender. Examples of such prosthetic femoral hip stems are described in U.S. patent application Ser. No. 12/028,377, entitled PROSTHETIC HIP IMPLANTS, filed on Feb. 8, 2008, U.S. patent application Ser. No. 11/687,862, entitled PROSTHETIC HIP IMPLANTS, filed on Mar. 19, 2007, and U.S. Provisional Patent Application Ser. No. 60/783,880, entitled PROSTHETIC HIP IMPLANTS, filed on Mar. 20, 2006, the disclosures of which are hereby expressly incorporated herein by reference.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system including set of rasps for preparing a bone to receive a prosthetic implant, the system comprising:
 a prosthetic implant having an outer surface geometry defining a size and a shape;
 a first rasp; and
 at least a second rasp;
 wherein the first and second rasps have a size and shape substantially congruent to the size and shape of the prosthetic implant, and
 wherein the first and second rasps differ in aggressiveness to achieve various levels of bone removal and bone compression,
 wherein each of the first and second rasps includes an anterior cutting surface, a posterior cutting surface, a medial cutting surface, a lateral cutting surface, and edges defined between the cutting surfaces, the first and second rasps having essentially identical cutting properties at corresponding edges and over corresponding portions of at least one of the medial and lateral cutting surfaces, the first rasp having more aggressive cutting properties than the second rasp over corresponding portions of at least one of the anterior and posterior cutting surfaces.

2. The system of claim 1, wherein the first rasp is a more aggressive rasp configured to achieve bone removal and the second rasp is a less aggressive rasp configured to achieve bone compression rather than bone removal.

3. The system of claim 1, wherein the first rasp has pointed teeth to achieve significant bone removal, and wherein the second rasp has at least one of:
 curved, rounded teeth to achieve bone removal, but to a lesser extent than the first rasp with pointed teeth;
 an essentially smooth face to achieve bone compression rather than bone removal; and
 a groove set into the essentially smooth face to achieve less bone compression than the essentially smooth face.

4. The system of claim 1, wherein the first rasp has at least one of:
 pointed teeth to achieve significant bone removal;
 curved, rounded teeth to achieve bone removal, but to a lesser extent than the pointed teeth;
 an essentially smooth face to achieve bone compression rather than bone removal; and a groove set into the essentially smooth face to achieve less bone compression than the essentially smooth face; and
wherein the second rasp has a different one of:
- pointed teeth to achieve significant bone removal;
- curved, rounded teeth to achieve bone removal, but to a lesser extent than the pointed teeth;
- an essentially smooth face to achieve bone compression rather than bone removal; and
- a groove set into the essentially smooth face to achieve less bone compression than the essentially smooth face.

5. The system of claim 1, wherein the first rasp has more cutting elements than the second rasp at least over corresponding portions of the first and second rasps.

6. The system of claim 1, wherein the first rasp has cutting elements of higher elevation and the second rasp has cutting elements of lower elevation at least over corresponding portions of the first and second rasps.

7. The system of claim 1, wherein the first rasp has a first elongate body with a geometry generally corresponding to the geometry of the prosthetic implant, and the second rasp has a second elongate body with a geometry generally corresponding to the geometry of the prosthetic implant, the first and second elongate bodies each comprising:
- a medial face having a medial profile generally corresponding to a medial profile of the prosthetic implant;
- a lateral face having a lateral profile generally corresponding to a lateral profile of the prosthetic implant;
- an anterior face having an anterior profile generally corresponding to an anterior profile of the prosthetic implant; and
- a posterior face having a posterior profile generally corresponding to a posterior profile of the prosthetic implant, the anterior face and the posterior face of the first elongate body having at least one of:
  - an essentially smooth face, whereby the essentially smooth face lacks teeth extending therefrom;
  - an essentially smooth face with a groove set into and interrupting the essentially smooth face;
  - a plurality of pointed teeth extending therefrom, whereby each pointed tooth extends from the face to an end defined between two essentially planar portions of the pointed tooth, each portion of the pointed tooth located within a plane, the planes intersecting along an axis, the end of the pointed tooth being located approximately 0.05 millimeters or less from the axis; and
  - a plurality of rounded teeth extending therefrom, whereby each rounded tooth extends from the face to an end defined between two essentially planar portions of the rounded tooth, each portion of the rounded tooth located within a plane, the planes intersecting along an axis, the end of the rounded tooth being located toward a longitudinal axis of the first elongate body more than approximately 0.05 millimeters from the axis;

wherein at least one of the anterior face and the posterior face of the second elongate body differs from the corresponding face of the first elongate body.

8. The system of claim 7, wherein the anterior face and the posterior face of the second elongate body have at least one of:
- an essentially smooth face, whereby the essentially smooth face lacks teeth extending therefrom;
- an essentially smooth face with a groove set into and interrupting the essentially smooth face;
- a plurality of pointed teeth extending therefrom, whereby each pointed tooth extends from the face to an end defined between two essentially planar portions of the pointed tooth, each portion of the pointed tooth located within a plane, the planes intersecting along an axis, the end of the pointed tooth being located approximately 0.05 millimeters or less from the axis; and
- a plurality of rounded teeth extending therefrom, whereby each rounded tooth extends from the face to an end defined between two essentially planar portions of the rounded tooth, each portion of the rounded tooth located within a plane, the planes intersecting along an axis, the end of the rounded tooth being located toward a longitudinal axis of the first elongate body more than approximately 0.05 millimeters from the axis.

9. The system of claim 1, further comprising a third rasp having a third elongate body with a geometry generally corresponding to the geometry of the prosthetic implant, the third elongate body comprising:
- a medial face having a medial profile generally corresponding to the medial profile of the prosthetic implant;
- a lateral face having a lateral profile generally corresponding to the lateral profile of the prosthetic implant;
- an anterior face having an anterior profile generally corresponding to the anterior profile of the prosthetic implant; and
- a posterior face having a posterior profile generally corresponding to the posterior profile of the prosthetic implant, at least one of the anterior face and the posterior face of the third elongate body differing from the corresponding faces of the first and second elongate bodies.

10. The system of claim 1, further comprising a third rasp generally corresponding to the size and shape of the prosthetic implant, wherein the aggressiveness of the third rasp differs from the aggressiveness of the first and second rasps.

* * * * *